United States Patent
Gramlich et al.

(10) Patent No.: US 9,975,994 B2
(45) Date of Patent: May 22, 2018

(54) DESALINATION OF POLYARYL ETHERS BY MEANS OF MELT EXTRACTION

(71) Applicant: BASF SE, Ludwingshafen (DE)

(72) Inventors: Simon Gramlich, Hirschberg (DE); Achim Stammer, Freinsheim (DE); Angela Ulzhöfer, Ludwigshafen (DE); Frank Niedermaier, Ladenburg (DE)

(73) Assignee: BASF SE (DE)

( * ) Notice: Subject to any disclaimer, the term of this patent is extended or adjusted under 35 U.S.C. 154(b) by 0 days. days.

(21) Appl. No.: 15/545,546

(22) PCT Filed: Jan. 22, 2016

(86) PCT No.: PCT/EP2016/051374
§ 371 (c)(1),
(2) Date: Jul. 21, 2017

(87) PCT Pub. No.: WO2016/116618
PCT Pub. Date: Jul. 28, 2016

(65) Prior Publication Data
US 2018/0009944 A1    Jan. 11, 2018

(30) Foreign Application Priority Data
Jan. 23, 2015    (EP) ..................................... 15152258

(51) Int. Cl.
| C08G 63/02 | (2006.01) |
| C08G 65/46 | (2006.01) |
| C07D 207/267 | (2006.01) |
| C07C 233/05 | (2006.01) |

(52) U.S. Cl.
CPC ............ *C08G 65/46* (2013.01); *C07C 233/05* (2013.01); *C07D 207/267* (2013.01)

(58) Field of Classification Search
CPC .................................................. A61B 17/155
USPC ................................................ 528/480, 481
See application file for complete search history.

(56) References Cited

U.S. PATENT DOCUMENTS

| 4,113,698 A | 9/1978 | Staniland |
| 4,200,727 A | 4/1980 | Blinne et al. |
| 4,200,728 A | 4/1980 | Blinne et al. |
| 5,013,816 A | 5/1991 | Bobbink et al. |
| 9,631,051 B2 | 4/2017 | Zhu et al. |
| 9,701,790 B2 | 7/2017 | Schmidt et al. |
| 9,738,756 B2 | 8/2017 | Haffner et al. |
| 2014/0256887 A1 | 9/2014 | Kory et al. |
| 2014/0256905 A1 | 9/2014 | Biedasek et al. |
| 2016/0009869 A1 | 1/2016 | Biedasek et al. |
| 2016/0130397 A1 | 5/2016 | Clauss et al. |
| 2016/0130398 A1 | 5/2016 | Zhu et al. |
| 2016/0145390 A1 | 5/2016 | Schmidt et al. |
| 2016/0159983 A1 | 6/2016 | Zhu et al. |
| 2016/0159990 A1 | 6/2016 | Erbes et al. |
| 2016/0325265 A1 | 11/2016 | Zhu et al. |
| 2016/0340509 A1 | 11/2016 | Schmidt et al. |
| 2017/0081472 A1 | 3/2017 | Zhu et al. |
| 2017/0081481 A1 | 3/2017 | Erbes et al. |

FOREIGN PATENT DOCUMENTS

| CN | 102786681 A | 11/2012 |
| DE | 1957091 A1 | 6/1970 |
| DE | 2749645 A1 | 5/1979 |
| DE | 3644464 A1 | 7/1988 |
| EP | 000361 A1 | 1/1979 |
| EP | 0292211 A2 | 11/1988 |
| EP | 2305740 A1 | 4/2011 |
| GB | 1264900 A | 2/1972 |
| GB | 2376019 A | 12/2002 |
| WO | WO-2010046482 A1 | 4/2010 |
| WO | WO-2014033321 A1 | 3/2014 |
| WO | WO-2014198756 A1 | 12/2014 |
| WO | WO-2016116616 A1 | 7/2016 |

OTHER PUBLICATIONS

International Search Report for PCT/EP2016/051374 dated May 9, 2016.
Written Opinion of the International Searching Authority for PCT/EP2016/051374 dated May 9, 2016.
English Translation of International Preliminary Report on Patentability for International Application No. PCT/EP2016/051374, dated Jul. 27, 2017.

*Primary Examiner* — Terressa Boykin
(74) *Attorney, Agent, or Firm* — Drinker Biddle & Reath LLP

(57) ABSTRACT

A method for desalinating a salt-containing polymer (SP) comprising a polyaryl ether having a softening temperature $T_S$ and a salt (S), comprising the steps of
  a) providing the salt-containing polymer (SP) at a first temperature $T_1$ above the softening temperature $T_S$ of the polyaryl ether,
  b) contacting the salt-containing polymer (SP) provided in step a) with an extractant (E) to obtain a desalinated polymer (DP) comprising the polyaryl ether, and a salt-containing extractant (SE) comprising the extractant (E) and the salt (S).

11 Claims, No Drawings

DESALINATION OF POLYARYL ETHERS BY MEANS OF MELT EXTRACTION

CROSS-REFERENCE TO RELATED APPLICATIONS

The application is a national stage application (under 35 U.S.C. § 371) of PCT/EP2016/051374, filed Jan. 22, 2016, which claims benefit of European Application No. 15152258.8, filed Jan. 23, 2015, both of which are incorporated herein by reference in their entirety.

The present invention relates to a method for desalinating a salt-containing polymer (SP) comprising a polyaryl ether and a salt (S), and to the desalinated polymer (DP) which comprises the polyaryl ether and is obtainable by this method.

A group of polyaryl ether polymers of particular economic significance is that of the polyaryl ether sulfones. Polyaryl ether polymers are part of the group of the high-performance thermoplastics and are notable for high heat distortion resistance combined with good mechanical properties and inherent flame retardancy.

The preparation of polyaryl ether polymers has long been known. The preparation of polyaryl ether polymers is generally effected by polycondensation of corresponding aromatic dihydroxyl compounds with aromatic dihalogen compounds, the polycondensation being conducted in an aprotic polar solvent in the presence of potassium carbonate as base. The polyaryl ether polymers are obtained in the production process in the form of a solution comprising the polyaryl ether polymers dissolved in the aprotic polar solvent. The potassium halide formed during the reaction can be separated from the solution by mechanical means, for example by centrifugation or filtration, such that the solution and hence also the subsequently isolated polyaryl ether polymers comprise only a small amount of or even no potassium halide. For subsequent isolation of the polyaryl ether polymers from the aprotic polar solvent, various methods are described in the prior art.

According to the methods described in DE 19 57 091 and EP 0 00 0361 for isolation of polyaryl ether polymers which are prepared by polycondensation in an aprotic polar solvent, the solution comprising the polyaryl ether polymers dissolved in an aprotic polar solvent is introduced into water and the polyaryl ether polymers are precipitated thereby.

DE 36 44 464 and EP 2 305 740 likewise describe processes for preparing polyaryl ether polymers by polycondensation in an aprotic polar solvent. The solution obtained, comprising the polyaryl ether polymers dissolved in the aprotic polar solvent, is subsequently dropletized in a precipitation bath comprising water, and the polyaryl ether polymers are thus obtained in the form of beads.

EP 0 292 211 describes a process for preparing aryl polyethers or thioethers, wherein a bisphenol, a bisthiophenol or a hydroxyphenyl mercaptan is contacted with a dihalobenzoid compound in the presence of a basic alkali metal catalyst, and wherein the conversion is effected in the presence of a solvent. The product solution obtained is contacted with water, and the alkali metal halide which forms in the reaction is thus removed.

U.S. Pat. No. 4,113,698 describes a process for preparing polyether ketones by nucleophilic polycondensation of an alkali metal bisphenoxide with at least one dihalo compound and/or an alkali metal halophenate in an aromatic solvent. The reaction mixture obtained is subsequently crystallized or precipitated and finally brought to a small particle size by grinding and washed with water.

WO 2010/046482 describes a process for preparing polyether ketones in diphenyl sulfone to obtain a reaction mixture which is then cooled such that it solidifies. The solid reaction mixture is then ground and extracted with acetone and water.

What is common to all the methods described in the prior art in which polyaryl ether polymers are prepared by polycondensation in an aprotic polar solvent is that they have only a low content of potassium halide. However, it is not possible to completely remove the aprotic polar solvent from the polyaryl ether polymers. These aprotic polar solvents are consequently also present in moldings which are produced from the polyaryl ether polymers obtainable by the processes described above.

DE 27 49 645 describes a method for preparing polyaryl ethers in a melt polymerization method by polycondensation of at least one bisphenol with at least one dihalobenzene compound or of a halophenol in the presence of anhydrous alkali metal carbonate in the absence of solvents or diluents. The reaction is conducted in a kneader or in an extruder. The inorganic constituents which are formed during the condensation reaction, for example sodium chloride or potassium chloride, are removed from the polyaryl ethers by dissolution and subsequent filtration, sieving or extraction.

WO 2014/033321 likewise describes a method for preparing aromatic polyaryl ethers in a melt polymerization method by reacting a dichlorodiphenyl sulfone component with a bisphenol component in the presence of an alkali metal carbonate in the absence of solvents or diluents, the reaction being conducted in a mixing kneader. The polyaryl ether polymers thus obtained are ground to a particle size of about 2 mm and washed twice with water at 80° C. for 3 hours in order to remove the alkali metal chloride formed as a by-product. However, the method described in WO 2014/033321 can remove only 80% of the alkali metal chloride from the polyaryl ether.

The polyaryl ether polymers prepared by melt polymerization do not have any residual content of aprotic polar solvent.

GB 2 376 019 describes a process for purifying polyketones. This involves contacting the polyketones with water and extractant. During the contacting, the polyketone is in the form of powders, pellets or granules.

CN 102 786 681 describes a process for purifying polymers, preferably polyether ketones. The polymer is used in solid form as a powder, in particulate form or in round form. It is then contacted with water as extractant.

It is thus an object of the present invention to provide an improved method for desalinating a salt-containing polymer (SP) comprising a polyaryl ether and a salt (S). The desalinated polymer (DP) thus prepared should have a low or zero residual content of aprotic polar solvents and a reduced residual content of salt (S) compared to the polyaryl ether polymers obtainable by the prior art methods. The method of the invention and the desalinated polymers (DP) obtainable thereby are to have the disadvantages of the methods described in the prior art and of the polymers obtainable therefrom only to a reduced degree, if at all. The method of the invention is to be simple, have a minimum susceptibility to faults and be performable inexpensively.

This object is achieved in accordance with the invention by a method for desalinating a salt-containing polymer (SP) comprising a polyaryl ether having a softening temperature $T_S$ and a salt (S), comprising the steps of a) providing the salt-containing polymer (SP) at a first temperature $T_1$ above the softening temperature $T_S$ of the polyaryl ether, b) contacting the salt-containing polymer (SP) provided in step a) with an extractant (E) to obtain a desalinated polymer (DP) comprising the polyaryl ether, and a salt-containing extractant (SE) comprising the extractant (E) and the salt (S), wherein step a) comprises the following steps)

i) providing a first salt-containing polymer (SP1) comprising the polyaryl ether and the salt (S), ii) pelletizing the first salt-containing polymer (SP1) provided in step i) to obtain a pelletized first salt-containing polymer (PSP1), iii) contacting the pelletized first salt-containing polymer (PSP1) obtained in step ii) with the extractant (E) to obtain the salt-containing polymer (SP) comprising the polyaryl ether and residues of the salt (S), and a first salt-containing extractant (SE1) comprising the extractant (E) and a portion of the salt (S), iv) heating the salt-containing polymer (SP) obtained in step iii) to a first temperature $T_1$ above the softening temperature $T_S$, preferably above the glass transition temperature T, of the polyaryl ether, and wherein step b) comprises the following step:

v) contacting the salt-containing polymer (SP) heated in step iv) with the extractant (E) to obtain the desalinated polymer (DP) comprising the polyaryl ether, and a second salt-containing extractant (SE2) comprising the extractant (E) and the residues of the salt (S), wherein the first salt-containing polymer (S1P) is provided in step i) by a melt polymerization method.

The present invention further provides a method for desalinating a salt-containing polymer (SP) comprising a polyaryl ether having a softening temperature $T_S$ and a salt (S), comprising the steps of a) providing the salt-containing polymer (SP) at a first temperature $T_1$ above the softening temperature $T_S$ of the polyaryl ether, b) contacting the salt-containing polymer (SP) provided in step a) with an extractant (E) to obtain a desalinated polymer (DP) comprising the polyaryl ether, and a salt-containing extractant (SE) comprising the extractant (E) and the salt (S).

It has been found that, surprisingly, the method of the invention, compared to the methods described in the prior art, can remove more salt (S) from the salt-containing polymer (SP) within the same period of time. This means that the salt (S) can be removed more quickly from the salt-containing polymer (SP). Surprisingly, the method of the invention can achieve a salt content of not more than 150 ppm by weight in the desalinated polymer (DP). This distinctly increases the storage stability of the desalinated polymer (DP) compared to the polyaryl ethers from the prior art which have been prepared by a melt polymerization process. The desalinated polymer (DP) additionally has good melt stability. In the course of remelting, there is thus neither degradation of the polyaryl ether nor progression of the polymerization of the polyaryl ether.

The polyaryl ether polymers have good storage stability. The polyaryl ether polymers obtained have good melt stability. In addition, the polyaryl ether polymers can frequently be used as membranes.

The method of the invention is also especially suitable for the desalination of salt-containing polymers (SP) which have been prepared by a melt polymerization process. If salt-containing polymers (SP) prepared by melt polymerization processes are used in the method of the invention, the desalinated polymers (DP) do not have any residual solvent content. Thus, the desalinated polymers (DP) thus obtainable are also usable for the production of moldings suitable for food applications. The moldings are very substantially harmless from a toxicological point of view.

The method of the invention is elucidated in detail hereinafter.

Salt-Containing Polymer (SP)

According to the invention, the salt-containing polymer (SP) comprises a polyaryl ether and a salt (S).

According to the invention, "a polyaryl ether" is understood to mean exactly one polyaryl ether or else mixtures of two or more polyaryl ethers.

According to the invention, "a salt (S)" is understood to mean exactly one salt (S) or else mixtures of two or more salts (S).

In one embodiment, the salt-containing polymer (SP) comprises at least 50% by weight, particularly preferably at least 60% by weight, more preferably at least 65% by weight and especially preferably at least 70% by weight of the polyaryl ether, based in each case on the total weight of the salt-containing polymer (SP).

In a further embodiment, the salt-containing polymer (SP) comprises at most 99.98% by weight, preferably at most 99% by weight, more preferably at most 90% by weight and especially preferably at most 80% by weight of the polyaryl ether, based in each case on the total weight of the salt-containing polymer (SP).

Preferably, the salt-containing polymer (SP) comprises 50% to 99.98% by weight, more preferably 60% to 99% by weight, especially preferably 65% to 90% by weight and most preferably 70% to 80% by weight of the polyaryl ether, based in each case on the total weight of the salt-containing polymer (SP).

In one embodiment, the salt-containing polymer (SP) comprises at least 0.02% by weight, preferably at least 1% by weight, more preferably at least 10% by weight and especially preferably at least 20% by weight of the salt (S), based in each case on the total weight of the salt-containing polymer (SP).

In a further embodiment, the salt-containing polymer (SP) comprises at most 50% by weight, preferably at most 40% by weight, more preferably at most 35% by weight and especially preferably at most 30% by weight of the salt (S), based in each case on the total weight of the salt-containing polymer (SP).

It is also preferable that the salt-containing polymer (SP) comprises 0.02% to 50% by weight of the salt (S), more preferably 1% to 40% by weight of the salt (S), especially preferably 10% to 35% by weight and most preferably 20% to 30% by weight of the salt (S), based in each case on the total weight of the salt-containing polymer (SP).

It is possible that the salt-containing polymer (SP) additionally comprises additives. Suitable additives are known as such to those skilled in the art. If the salt-containing polymer (SP) additionally comprises additives, the salt-containing polymer (SP) generally comprises 0.01% to 10% by weight of additives, preferably 0.01% to 7% by weight of additives and especially preferably 0.01% to 5% by weight of additives, based in each case on the total weight of the salt-containing polymer (SP). In one embodiment, the salt-containing polymer (SP) does not comprise any additional additives.

In addition, the salt-containing polymer (SP) may comprise a carbonate compound (C). With regard to the carbonate compound (C), the details and preferences described further down apply. If the salt-containing polymer (SP) comprises a carbonate compound (C), the salt-containing polymer (SP) comprises in the range from 0.01% to 20% by weight, preferably in the range from 0.01% to 5% by weight and especially preferably in the range from 0.01% to 2% by weight of the carbonate compound (C), based on the total weight of the salt-containing polymer (SP). The carbonate compound (C) is different than the salt (S). In one embodiment, the salt-containing polymer (SP) does not comprise any carbonate compounds (C).

"A carbonate compound (C)" in the context of the present invention means either exactly one carbonate compound (C) or a mixture of two or more carbonate compounds (C).

In a further embodiment, the salt-containing polymer (SP) comprises 50% to 99.98% by weight of the polyaryl ether and 0.02% to 50% by weight of the salt (S), preferably 60% to 99% by weight of the polyaryl ether and 1% to 40% by weight of the salt (S), especially preferably 65% to 90% by weight of the polyaryl ether and 10% to 35% by weight of the salt (S) and most preferably 70% to 80% by weight of the polyaryl ether and 20% to 30% by weight of the salt (S), based in each case on the total weight of the salt-containing polymer (SP). In general, the sum totals of the percentages by weight of the polyaryl ether, the salt (S) and any additional additives and carbonate compound (C) add up to 100%.

The viscosity numbers of the salt-containing polymer (SP) are generally in the range from 30 to 120 mL/g, preferably from 35 to 110 mL/g and especially preferably from 40 to 100 mL/g, determined by Ubbelohde viscosity number measurement of a 0.01 g/mL solution of the salt-containing polymer (SP) in a 1:1 phenol/1,2-dichlorobenzene mixture in accordance with DIN 51562.

In a further preferred embodiment of the present invention, the viscosity numbers of the salt-containing polymer (SP) are in the range from 15 to 900 mL/g, preferably from 22.5 to 75 mL/g and especially preferably from 26.25 to 71.25 mL/g, determined by Ubbelohde viscosity number measurement of a 0.01 g/mL solution of the salt-containing polymer (SP) in a 1:1 phenol/1,2-dichlorobenzene mixture in accordance with DIN 51562.

In general, the salt (S) comprises a cation and a halide, preferably a cation and a chloride. A halide is also referred to as "halide anion". A chloride is also referred to as "chloride anion".

According to the invention, "a cation" is understood to mean exactly one cation or else mixtures of two or more cations.

According to the invention, "a halide" is understood to mean exactly one halide or else mixtures of two or more halides.

The percentages by weight of the salt (S) in the salt-containing polymer (SP) can therefore be determined via the measurement of the percentages by weight of the halide, preferably of the chloride, in the salt-containing polymer (SP). The percentages by weight of the halide are understood to mean the percentages by weight of the anionic halogen, i.e. the percentages by weight of the free halide and not the percentages by weight of the polymer-bound halogen. The same applies to the percentages by weight of chloride. These relate to the percentages by weight of the ionic chlorine and hence to the percentages by weight of the free chloride and not to the percentages by weight of the polymer-bound chlorine.

To determine the percentages by weight of halide, preferably of chloride, in the salt-containing polymer (SP), 700 mg of the salt-containing polymer (SP) are dissolved in N-methylpyrrolidone (NMP) and the resulting solution is diluted with an acetic acid/acetone mixture (ratio of acetic acid to acetone 1:1). The solution thus obtained is acidified with sulfuric acid or nitric acid and then potentiometrically titrated with a 0.0002 mol/L silver nitrate solution, using methyl orange as indicator. The electrode used is an Ag Titrode from Metrohm.

The percentages by weight of halide can subsequently be used to calculate the percentages by weight of the cation likewise present in the salt (S) in the salt-containing polymer (SP). Methods for this purpose are known to those skilled in the art. The sum total of the percentages by weight of the halide and of the percentages by weight of the cation in the salt-containing polymer then gives the percentages by weight of the salt (S) in the salt-containing polymer (SP).

The percentages by weight of salt (S) in the pre-desalinated polymer (PDP) described hereinafter and the desalinated polymer (DP) are determined in the same manner in accordance with the invention.

Polyaryl ethers are known to those skilled in the art as a polymer class. Useful polyaryl ethers for use in the method of the invention are in principle any which are known to those skilled in the art and/or preparable by known methods. Corresponding methods for preparation are elucidated further down.

Preferred polyaryl ethers are formed from units of the general formula (I):

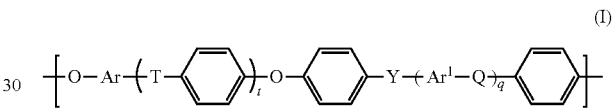

(I)

where the symbols t, q, Q, T, Y, Ar and $Ar^1$ are defined as follows:

t, q: each independently 0, 1, 2 or 3,

Q, T, Y: each independently a chemical bond or group selected from —O—, —S—, —$SO_2$—, S=O, C=O, —N=N— and —$CR^aR^b$— where $R^a$ and $R^b$ are each independently a hydrogen atom or a $C_1$-$C_{12}$-alkyl, $C_1$-$C_{12}$-alkoxy or $C_6$-$C_{18}$-aryl group, and where at least one of Q, T and Y is —$SO_2$— and Ar, $Ar^1$: each independently an arylene group having from 6 to 18 carbon atoms.

If Q, T or Y, under the abovementioned conditions, is a chemical bond, this is understood to mean that the adjacent group to the left and the adjacent group to the right are bonded directly to one another via a chemical bond.

Preferably, however, Q, T and Y in formula I are each independently selected from —O— and —$SO_2$—, with the proviso that at least one of the group consisting of Q, T and Y is —$SO_2$—. These polyaryl ethers are polyaryl ether sulfones.

The present invention thus also provides a method in which the polyaryl ether is a polyaryl ether sulfone.

If Q, T or Y is —$CR^aR^b$—, $R^a$ and $R^b$ are each independently a hydrogen atom or a $C_1$-$C_{12}$-alkyl, $C_1$-$C_{12}$-alkoxy or $C_6$-$C_{18}$-aryl group.

Preferred $C_1$-$C_{12}$-alkyl groups comprise linear and branched, saturated alkyl groups having from 1 to 12 carbon atoms. Particular mention should be made of the following radicals: $C_1$-$C_6$-alkyl radical such as methyl, ethyl, n-propyl, i-propyl, n-butyl, sec-butyl, 2- or 3-methylpentyl and longer-chain radicals such as unbranched heptyl, octyl, nonyl, decyl, undecyl, lauryl and the singly or multiply branched analogs thereof.

Useful alkyl radicals in the aforementioned usable $C_1$-$C_{12}$-alkoxy groups include the alkyl groups defined further up having from 1 to 12 carbon atoms. Cycloalkyl radicals usable with preference include especially $C_3$-$C_{12}$-cycloalkyl radicals, for example cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclopentylethyl, -propyl, -butyl, -pentyl, -hexyl, cyclohexylmethyl, -dimethyl, and -trimethyl.

Ar and $Ar^1$ are each independently a $C_6$-$C_{10}$-arylene group. Proceeding from the starting materials described below, Ar is preferably derived from an electron-rich aromatic substance subject to easy electrophilic attack, preferably selected from the group consisting of hydroquinone, resorcinol, dihydroxynaphthalene, especially 2,7-dihydroxynaphthalene, and 4,4'-bisphenol. $Ar^1$ is preferably an unsubstituted $C_6$- or $C_{12}$-arylene group.

Useful $C_6$-$C_{18}$-arylene groups Ar and $Ar^1$ include in particular phenylene groups such as 1,2-, 1,3- and 1,4-phenylene, naphthylene groups, for example 1,6-, 1,7-, 2,6- and 2,7-naphthylene, and the arylene groups derived from anthracene, phenanthrene and naphthacene.

Preferably, Ar and $Ar^1$ in the preferred embodiment of formula (I) are each independently selected from the group consisting of 1,4-phenylene, 1,3-phenylene, naphthylene, especially 2,7-dihydroxynaphthylene, and 4,4'-bisphenylene.

Preferred polyaryl ethers are those comprising at least one of the following units Ia to Io as repeat structural units:

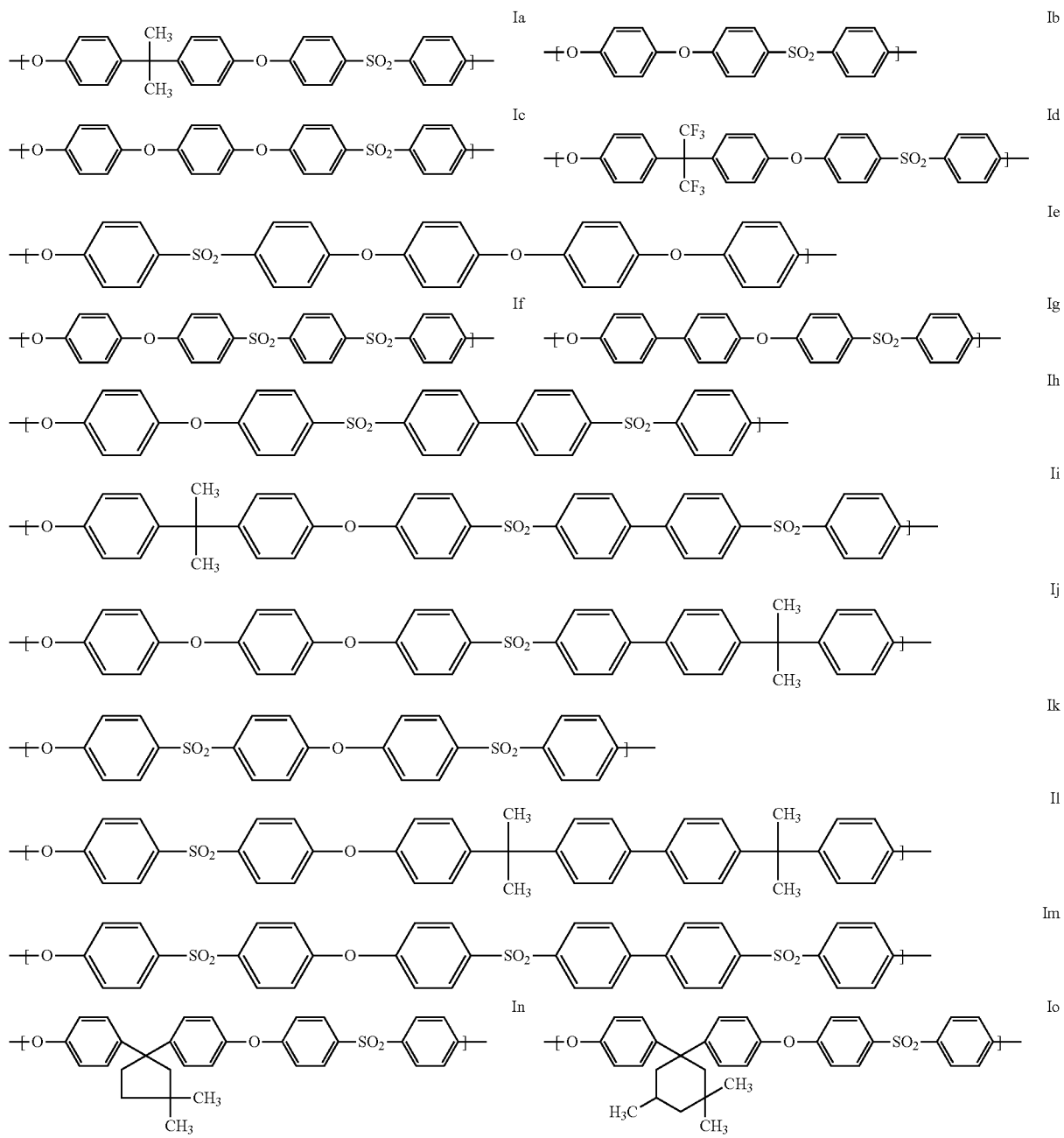

In addition to the preferred units Ia to Io, preference is also given to those units in which one or more 1,4-phenylene units which originate from hydroquinone are replaced by 1,3-phenylene units which originate from resorcinol or by naphthylene units which originate from dihydroxynaphthalene.

Particularly preferred units of the general formula (I) are the units Ia, Ig and Ik. It is also particularly preferred when the polyaryl ethers are formed essentially from one kind of units of the general formula (I), especially from a unit selected from Ia, Ig and Ik.

In a particularly preferred embodiment, Ar=1,4-phenylene, t=1, q=0, T is a chemical bond and Y=$SO_2$. Particularly preferred polyaryl ether sulfones formed from the aforementioned repeat unit are referred to as polyphenylene sulfone (PPSU) (formula Ig).

In a further particularly preferred embodiment, Ar=1,4-phenylene, t=1, q=0, T=$C(CH_3)_2$ and Y=$SO_2$. Particularly preferred polyaryl ether sulfones formed from the aforementioned repeat unit are referred to as polysulfone (PSU) (formula Ia).

In a further particularly preferred embodiment, Ar=1,4-phenylene, t=1, q=0, T=Y=$SO_2$. Particularly preferred polyaryl ether sulfones formed from the aforementioned repeat unit are referred to as polyether sulfone (PESU) (formula Ik).

Abbreviations such as PPSU, PSU and PESU in the context of the present invention conform to DIN EN ISO 1043-1 (Plastics—Symbols and abbreviated terms—Part 1: Basic polymers and their special characteristics (ISO 1043-1:2001); German version EN ISO 1043-1:2002).

The polyaryl ethers preferably have weight-average molecular weights $M_w$ of 10 000 to 150 000 g/mol, especially of 15 000 to 120 000 g/mol, more preferably of 18 000 to 100 000 g/mol, determined by means of gel permeation chromatography in a dimethylacetamide solvent against narrow-distribution polymethylmethacrylate as standard.

The polyaryl ethers preferably have a number-average molecular weight $M_n$ of 10 000 to 35 000 g/mol, determined by means of gel permeation chromatography in a dimethylacetamide solvent against narrow-distribution polymethylmethacrylate as standard.

The polydispersity is preferably from 1.9 to 7.5, more preferably from 2.1 to 4, In addition, the polyaryl ethers in pure substance preferably have an apparent melt viscosity at 350° C./1150 $s^{-1}$ of 100 to 1000 Pa s, preferably of 150 to 300 Pa s and especially preferably of 150 to 275 Pa s.

The melt viscosity was determined by means of a capillary rheometer. The apparent viscosity was determined at 350° C. as a function of the shear rate in a capillary viscometer (Götffert Rheograph 2003 capillary viscometer) with a circular capillary of length 30 mm, a radius of 0.5 mm, a nozzle inlet angle of 180°, a diameter of the reservoir vessel for the melt of 12 mm and with a preheating time of 5 minutes. The values reported are those determined at 1150 $s^{-1}$.

The softening temperature $T_S$ of the polyaryl ether is typically in the range from 150 to 230° C., preferably in the range from 155 to 230° C. and especially preferably in the range from 160 to 180° C., determined by means of dynamic differential calorimetry. Methods for this purpose are known to those skilled in the art.

The softening temperature $T_S$ of the polyaryl ether is understood in the present context to mean the glass transition temperature of the pure polyaryl ether comprising 2% to 30% by weight of the extractant (E), based on the total weight of the polyaryl ether and the extractant (E), where the polyaryl ether does not contain any salt (S).

The softening temperature $T_S$ of the polyaryl ether is preferably understood in the present context to mean the glass transition temperature of the pure polyaryl ether comprising 15% by weight of the extractant (E), based on the total weight of the polyaryl ether and the extractant (E), where the polyaryl ether does not contain any salt (S).

The softening temperature $T_S$ of the polyaryl ether can therefore be determined analogously to the glass transition temperature $T_G$ of the polyaryl ether.

It will be appreciated that the softening temperature $T_S$ of the polyaryl ether is below the glass transition temperature $T_G$ of the polyaryl ether.

The present invention thus further provides a method in which the softening temperature $T_S$ of the polyaryl ether is in the range from 150 to 230° C.

The glass transition temperature $T_G$ of the polyaryl ether is typically in the range from 160 to 270° C., preferably in the range from 170 to 250° C. and especially preferably in the range from 180 to 230° C., determined by differential thermoanalysis (DTA; differential calorimetry, DSC).

Methods for determining glass transition temperature $T_G$ by differential thermoanalysis are known as such to those skilled in the art.

The glass transition temperature $T_G$ is understood to mean the temperature at which the polyaryl ether solidifies in the course of cooling to give a glassy solid.

The present invention thus further provides a method in which the glass transition temperature $T_G$ of the polyaryl ether is in the range from 160° C. to 270° C.

The melting temperature $T_M$ of the polyaryl ether is typically in the range from 200 to 300° C. and preferably in the range from 230 to 280° C., determined by differential thermoanalysis (DTA; differential scanning calorimetry, DSC).

The melting temperature $T_M$ of the polyaryl ether is understood to mean the temperature at which a semicrystalline polyaryl ether is converted fully from the solid state of matter to the liquid state of matter, and the polyaryl ether is thus completely in the form of a melt.

It will be clear to the person skilled in the art that, in the case of an amorphous polyether, the melting temperature $T_M$ of the polyaryl ether is the same as the glass transition temperature $T_G$ of the polyaryl ether.

Preparation methods which lead to the aforementioned polyaryl ethers are known per se to those skilled in the art and are described, for example, in Herman F. Mark, "Encyclopedia of Polymer Science and Technology", third edition, Volume 4, 2003, "Polysulfones" chapter on pages 2 to 8, and in Hans R. Kricheldorf, "Aromatic Polyethers" in: Handbook of Polymer Synthesis, second edition, 2005, on pages 427 to 443.

Polyaryl ethers are preferably prepared by the reaction of a component (a1) comprising at least one aromatic dihydroxyl compound and a component (a2) comprising at least one aromatic sulfone compound having two halogen substituents. The molar ratio of components (a1) to (a2) is preferably in the range from 0.99 to 1.4, more preferably in the range from 1.0 to 1.2 and most preferably in the range from 1.0 to 1.1.

The reaction is typically conducted in the presence of a carbonate compound (C).

Component (a1) comprises at least one aromatic dihydroxyl compound. Component (a1) especially comprises the following compounds:
4,4'-dihydroxybiphenyl;

dihydroxybenzenes, especially hydroquinone and resorcinol;

dihydroxynaphthalenes, especially 1,5-dihydroxynaphthalene, 1,6-dihydroxynaphthalene, 1,7-dihydroxynaphthalene and 2,7-dihydroxynaphthalene;

dihydroxybiphenyls other than 4,4'-biphenol, especially 2,2'-biphenol;

bisphenyl ethers, especially bis(4-hydroxyphenyl) ether and bis(2-hydroxyphenyl) ether;

bisphenylpropanes, especially 2,2-bis(4-hydroxyphenyl) propane, 2,2-bis(3-methyl-4-hydroxyphenyl)propane and 2,2-bis(3,5-dimethyl-4-hydroxyphenyl)propane;

bisphenylmethanes, especially bis(4-hydroxyphenyl)methane;

bisphenylcyclohexanes, especially bis(4-hydroxyphenyl)-2,2,4-trimethylcyclohexane;

bisphenyl sulfones, especially bis(4-hydroxyphenyl) sulfone;

bisphenyl sulfides, especially bis(4-hydroxyphenyl) sulfide;

bisphenyl ketones, especially bis(4-hydroxyphenyl) ketone;

bisphenylhexafluoropropanes, especially 2,2-bis(3,5-dimethyl-4-hydroxyphenyl)hexafluoropropane; and bisphenylfluorenes, especially 9,9-bis(4-hydroxyphenyl) fluorene.

Preferably, component (a1) comprises at least 50% by weight, more preferably at least 60% by weight, particularly preferably at least 80% by weight and especially at least 95% by weight of at least one dihydroxyl component selected from the group consisting of 4,4'-dihydroxybiphenyl, 2,2-bis(4-hydroxyphenyl)propane and bis(4-hydroxyphenyl) sulfone, based in each case on the total weight of component (a1). Most preferably, component (a1) consists of at least one dihydroxyl component selected from the group consisting of 4,4'-dihydroxybiphenyl, 2,2-bis(4-hydroxyphenyl)propane and bis(4-hydroxyphenyl) sulfone.

2,2-Bis(4-hydroxyphenyl)propane is also known by the name bisphenol A. Bis(4-hydroxyphenyl) sulfone is also known by the name bisphenol S.

Preferably, component (a2) comprises at least 50% by weight, preferably at least 60% by weight, more preferably at least 80% by weight and especially at least 95% by weight of at least one aromatic sulfone compound having two halogen substituents, based in each case on the total weight of component (a2).

Aromatic sulfone compounds having two halogen substituents that are suitable as component (a2) are known in principle to those skilled in the art. Preferred components (a2) are especially dihalodiphenyl sulfones such as 4,4'-dichlorodiphenyl sulfone, 4,4'-difluorodiphenyl sulfone, 4,4'-dibromodiphenyl sulfone, 2,2'-dichlorodiphenyl sulfone and 2,2'-difluorodiphenyl sulfone. 4,4'-Dichlorodiphenyl sulfone and 4,4'-difluorodiphenyl sulfone are particularly preferred. Very particular preference is given to 4,4'-dichlorodiphenyl sulfone.

The reaction of 4,4'-dihydroxybiphenyl as component (a1) and 4,4'-dihalodiphenyl sulfone as component (a2) gives polyphenylene sulfone (PPSU) as polyaryl ether sulfone (formula Ig).

The reaction of bisphenol A as component (a1) and 4,4'-dihalodiphenyl sulfone as component (a2) gives polysulfone (PSU) as polyaryl ether sulfone (formula Ia).

The reaction of bisphenol S as component (a1) and 4,4'-dihalodiphenyl sulfone as component (a2) gives polyether sulfone (PESU) as polyaryl ether sulfone (formula Ik).

Preferred polyaryl ether sulfones are polyphenylene sulfone (PPSU) and polyether sulfone (PESU).

The polyaryl ethers may have a number of different end groups. For example, they may have hydroxide end groups, halogen end groups and/or alkoxide end groups. If the polyaryl ethers, after the production process, are reacted with an etherifying agent, the polyaryl ethers may also have ether end groups. Suitable etherifying agents are known to those skilled in the art and are, for example, organic monohalogen compounds.

Preferred etherifying agents are selected from the group consisting of chloromethane, bromomethane, iodomethane and dimethyl carbonate.

Suitable carbonate compounds (C) are known as such to those skilled in the art. Preferred carbonate compounds (C) are alkali metal carbonates and/or alkaline earth metal carbonates. Preferably, the carbonate compounds (C) are anhydrous. Suitable carbonate compounds (C) are especially anhydrous alkali metal carbonate, preferably anhydrous sodium carbonate, anhydrous potassium carbonate or mixtures thereof, very particular preference being given to anhydrous potassium carbonate.

The salt-containing polymer (SP) comprising the polyaryl ether and the salt (S) can be prepared in the presence of a solvent or diluent; preparation is likewise possible in the absence of a solvent or diluent. Preference is given to preparation in the absence of a solvent or diluent. Particular preference is given to preparation in the absence of a solvent or diluent as a melt polymerization method.

Methods for preparing polyaryl ethers in the presence of a solvent or diluent are known as such to those skilled in the art. In one embodiment of the invention, they can also be used for preparation of the salt-containing polymer (SP). For this purpose, component (a1) and component (a2) are converted in an aprotic polar solvent in the presence of a carbonate compound (C). The solvent may optionally also comprise an azeotroping agent which forms an azeotrope with the water formed in the condensation reaction. Suitable aprotic polar solvents are, for example, selected from the group consisting of N,N-dimethylformamide, N,N-dimethylacetamide, N-methylpyrrolidone, N-ethylpyrrolidone, dimethyl sulfoxide, dimethyl sulfone, sulfolane and diphenyl sulfone. Suitable azeotroping agents are, for example, toluene and/or chlorobenzene.

The salt-containing polymers (SP) thus prepared can then be precipitated, for example, in water by methods known to those skilled in the art.

In a preferred embodiment, the salt-containing polymers (SP) are prepared in the absence of solvents or diluents. They are more preferably prepared in a melt polymerization process. Melt polymerization processes for polyaryl ethers are described, for example, in DE 2 749 645 and in WO 2014/033321 and can be used in a preferred embodiment of the present invention for preparation of the salt-containing polymer (SP).

The present invention thus also provides a process in which the salt-containing polymer (SP) is prepared by a melt polymerization method.

The melt polymerization can be performed as a batchwise process or as a continuous process. Preference is given to performance as a continuous process.

Suitable reactors are all known reactor types which are suitable for mixing high-viscosity materials and also allow removal of gaseous condensation products and heating of the monomers above the melting point thereof. Preferred reactors are extruders or mixing kneaders, particular preference being given to mixing kneaders. Preference is also given to single- or twin-shaft kneaders, particular preference being given to twin-shaft kneaders. It is further preferable that the mixing kneader is additionally equipped with a reflux condenser in order to recycle volatile monomer which may have evaporated at the reaction temperatures into the mixing kneader.

Typically, the melt polymerization is conducted at a temperature below the decomposition temperature of the polyaryl ether. Preferably, the temperature in the melt polymerization is at least 1° C., preferably at least 5° C. and especially preferably at least 10° C. below the decomposition temperature of the polyaryl ether.

In general, the melt polymerization is conducted at a temperature in the range from 200 to 400° C., preferably in the range from 250 to 350° C.

In one embodiment, component (a1) and component (a2) are initially charged in the mixing kneader in a molar ratio of 0.9 to 1.4, preferably of 1.0 to 1.2 and especially preferably of 1.0 to 1.1. The carbonate compound (C) is then added as a separate component. Preferably, the carbonate compound (C) is fed in in a molar ratio relative to component (a1) of 0.9 to 1.22, preferably of 1.0 to 1.12 and especially preferably of 1.03 to 1.10.

If component (a1) and component (a2) are initially charged in the mixing kneader, it is preferable that components (a1) and (a2) are first melted and then the carbonate compound (C) is fed in. Preferably, components (a1) and (a2) are mixed with one another and melted and only then fed to the mixing kneader.

It is also possible to initially charge the carbonate compound (C) with one of the two components (a1) and (a2) and then to add the second of the two components (a1) and (a2). It is especially preferable to initially charge the carbonate compounds (C) with component (a1). In that case, component (a1) is generally reacted with the carbonate compound (C) to form a dialkoxide and then component (a2) is added.

With regard to the molar ratio of the two components (a1) and (a2) and the carbonate compound (C), the above-described details and preferences apply, even when the carbonate compound (C) is initially charged with one of the two components (a1) and (a2).

Component (a1) and/or (a2) can be introduced into the mixing kneader in liquid or solid form.

In another embodiment of the present invention, components (a1) and (a2) and the carbonate compound (C) are first mixed as a powder and then fed to the mixing kneader. In the mixing kneader they are then melted and converted.

The reaction time in the reactor is generally 0.5 to 3.5 hours, preferably 1 to 2 hours.

In another embodiment, the reaction time in the reactor is 0.5 to 3.5 hours, preferably 1.5 to 3 hours.

In the reaction of component (a1) with component (a2) in the presence of the carbonate compound (C), condensation products formed in addition to the polyaryl ether are water, carbon dioxide and the salt (S). The water formed and the carbon dioxide formed can be removed from the reactor as gaseous constituents during the reaction. The salt (S) generally remains in the polyaryl ether when the salt-containing polymer (SP) is obtained. In general, the salt (S) is an inorganic salt when the carbonate compound (C) used is an inorganic carbonate compound (C). Preferably, the salt (S) is an alkali metal halide when the carbonate compound (C) used is an alkali metal carbonate. Most preferably, the salt (S) is potassium chloride and/or sodium chloride when the carbonate compound (C) used is potassium carbonate and/or sodium carbonate.

The present invention thus also provides a method in which the salt (S) comprises an inorganic salt.

The present invention further provides a method in which the salt (S) comprises potassium chloride and/or sodium chloride.

The salt (S) generally has a particle size in the range from 0.1 to 100 μm, preferably in the range from 0.5 to 50 μm, more preferably in the range from 0.8 to 30 μm and most preferably in the range from 1 to 10 μm. The particle size is determined by SEM (scanning electron microscopy) imaging at an acceleration voltage of 8 kV.

The salt (S) is generally dispersed in particulate form in the salt-containing polymer (SP).

Step a)

In step a), the salt-containing polymer (SP) is provided at a first temperature $T_1$ above the softening temperature $T_S$ of the polyaryl ether.

Preferably, the first temperature $T_1$ is above the glass transition temperature $T_G$ of the polyaryl ether.

The first temperature $T_1$ is typically at least 1° C., preferably at least 5° C. and especially preferably at least 10° C. above the softening temperature $T_S$ of the polyaryl ether.

In a further preferred embodiment, the first temperature $T_1$ is at least 1° C., preferably at least 5° C. and especially preferably at least 10° C. above the glass transition temperature $T_G$ of the polyaryl ether.

The first temperature $T_1$ is below the decomposition temperature of the polyaryl ether. Preferably, the first temperature $T_1$ is at least 1° C., preferably at least 5° C. and especially preferably at least 10° C. below the decomposition temperature of the polyaryl ether.

In a preferred embodiment, the first temperature $T_1$ is within a range from 160 to 300° C., preferably in the range from 200 to 280° C. and especially preferably in the range from 220 to 260° C.

The present invention thus further provides a method in which the first temperature $T_1$ in step a) is within a range from 160 to 300° C.

It is also preferable in accordance with the invention that the first temperature $T_1$ is in the range from 1 to 100° C., preferably in the range from 5 to 50° C. and especially preferably in the range from 20 to 50° C. above the glass transition temperature $T_G$ of the polyaryl ether.

The present invention thus also provides a method in which the first temperature $T_1$ is in the range from 1 to 100° C. above the softening temperature $T_S$ of the polyaryl ether.

The first temperature $T_1$ may also be above the melting temperature $T_M$ of the polyaryl ether. When the first temperature $T_1$ is above the melting temperature $T_M$ of the polyaryl ether, the salt-containing polymer (SP) is provided in step a) as a melt.

In step a), the salt-containing polymer (SP) can be provided in any desired reactor which enables the salt-containing polymer (SP) to be kept at the first temperature $T_1$.

Reactors of this kind are known to those skilled in the art. Suitable reactors are, for example, stirred tank reactors, autoclaves, kneaders, extruders or thin-film evaporators.

The reactor may also comprise dynamic or static mixing elements. Dynamic and static mixing elements as such are known to those skilled in the art. Dynamic mixing elements are, for example, stirrers such as propeller stirrers, paddle stirrers, anchor stirrers and self-cleaning twin-shaft mixing elements.

The salt-containing polymer (SP) can be provided in step a) by any methods known to those skilled in the art. For example, the salt-containing polymer (SP) can first be prepared in a continuous or batchwise process as described above and then processed to give solid powder, for example in the form of granules or powder. The salt-containing polymer (SP) can then be provided in step a) by heating the solid powder of the salt-containing polymer (SP) to the first temperature $T_1$.

In addition, it is possible to provide the salt-containing polymer (SP) directly after it has been prepared, preferably after it has been prepared by a melt polymerization method, especially preferably after it has been prepared by melt polymerization, in a continuous method in step a). In that case, the salt-containing polymer (SP) is generally provided directly after it has been prepared in step a), preferably by providing the melt of the salt-containing polymer (SP) as obtained in the preparation in step a) without prior processing of the salt-containing polymer (SP) to give a solid powder. This embodiment is preferred.

Step b)

In step b), the salt-containing polymer (SP) provided in step a) is contacted with an extractant (E), and a desalinated polymer (DP) comprising the polyaryl ether, and a salt-containing extractant (SE) comprising the extractant (E) and the salt (S) are obtained.

Step b) is an extraction. The terms "step b)" and "extraction" are therefore used synonymously hereinafter.

Preferably, step b) is conducted directly after step a).

The extractant (E) used may be exactly one extractant. It is likewise possible to use a mixture of two or more extractants.

A suitable extractant (E) is in principle any solvent that dissolves the salt (S). Preferably, the extractant (E) comprises a protic solvent. More preferably, the extractant (E) comprises water.

The present invention thus also provides a process in which the extractant (E) used is a protic solvent.

In general, the extractant (E) comprises at least 50% by weight, preferably at least 70% by weight, especially preferably at least 80% by weight and most preferably at least 90% by weight of water, based in each case on the total weight of the extractant (E).

The present invention thus also provides a process in which the extractant (E) in step b) comprises water.

The salt-containing polymer (SP) is generally contacted with the extractant (E) in a reactor. Suitable reactor types for this purpose are in principle any which are known to those skilled in the art and which are suitable for use at the pressures and temperatures used in step b). For example, the salt-containing polymer (SP) is contacted with the extractant (E) in step b) in the same reactor in which the salt-containing polymer (SP) was provided at the first temperature $T_1$ in step a).

In that case, the details and preferences described above for the reactor in step a) apply to the reactor in step b). Preferably, the salt-containing polymer (SP) is contacted continuously with the extractant (E) in step b) in a dynamic mixer. Methods for this purpose are known to those skilled in the art.

The salt-containing polymer (SP) is preferably contacted with the extractant (E) in step b) at a second temperature $T_2$ above the softening temperature $T_S$, preferably above the glass transition temperature $T_G$, of the polyaryl ether.

Typically, the second temperature $T_2$ is at least 1° C., preferably at least 5° C. and especially preferably at least 10° C. above the softening temperature $T_S$, preferably the glass transition temperature $T_G$, of the polyaryl ether.

The present invention thus also provides a method in which the salt-containing polymer (SP) is contacted with the extractant (E) in step b) at a second temperature $T_2$ above the softening temperature $T_S$ of the polyaryl ether.

The second temperature $T_2$ is below the decomposition temperature of the polyaryl ether. Preferably, the second temperature $T_2$ is at least 1° C., preferably at least 5° C. and especially preferably at least 10° C. below the decomposition temperature of the polyaryl ether.

The second temperature $T_2$ at which the salt-containing polymer (SP) is contacted with the extractant (E) in step b) is, for example, in the range from 160 to 300° C., preferably in the range from 200 to 280° C. and especially preferably in the range from 220 to 260° C.

The present invention thus also provides a method in which the second temperature $T_2$ at which the salt-containing polymer (SP) is contacted with the extractant (E) in step b) is in the range from 160 to 300° C.

The second temperature $T_2$ may be above the first temperature $T_1$, and the second temperature $T_2$ may equally be below the first temperature $T_1$, in each case under the condition that the first temperature $T_1$ and the second temperature $T_2$ are above the softening temperature $T_S$, preferably above the glass transition temperature $T_G$ and below the decomposition temperature, of the polyaryl ether. In one embodiment of the method of the invention, the second temperature $T_2$ is equal to the first temperature $T_1$.

The present invention thus also provides a method in which the salt-containing polymer (SP) provided in step a) is contacted with the extractant (E) in step b) at the first temperature $T_1$. This embodiment is preferred.

The pressure in step b) is typically in the range from 6 to 100 bar, preferably in the range from 10 to 70 bar and especially preferably in the range from 20 to 50 bar.

The present invention thus also provides a method in which the salt-containing polymer (SP) provided in step a) is contacted with the extractant (E) in step b) at a pressure in the range from 6 to 100 bar.

In step b), the desalinated polymer (DP) and the salt-containing extractant (SE) are obtained.

The salt-containing extractant (SE) obtained in step b) comprises the portion of the salt (S) which has been removed from the salt-containing polymer (SP). In general, the salt-containing extractant (SE) comprises 0.1% to 20% by weight of the salt (S), preferably 0.5% to 10% by weight and especially preferably 1% to 5% by weight of the salt (S), based in each case on the total weight of the salt-containing extractant (SE).

In a further preferred embodiment of the present invention, the provision of the salt-containing polymer (SP) in method step a) comprises the following steps i) to iv):

i) providing a first salt-containing polymer (SP1) comprising the polyaryl ether and the salt (S), ii) pelletizing the first salt-containing polymer (SP1) provided in step i) to obtain a pelletized first salt-containing polymer (PSP1), iii) contacting the pelletized first salt-containing polymer (PSP1) obtained in step ii) with the extractant (E) to obtain the salt-containing polymer (SP) comprising the polyaryl ether and residues of the salt (S), and a first salt-containing extractant (SE1) comprising the extractant (E) and a portion of the salt (S), iv) heating the salt-containing polymer (SP) obtained in step iii) to a first temperature $T_1$ above the softening temperature $T_S$, preferably above the glass transition temperature $T_G$ of the polyaryl ether, and method step b) comprises the following step v)

v) contacting the salt-containing polymer (SP) heated in step iv) with the extractant (E) to obtain the desalinated polymer (DP) comprising the polyaryl ether, and a second salt-containing extractant (SE2) comprising the extractant (E) and the residues of the salt (S).

The present invention thus also provides a process comprising the steps of:
i) providing a first salt-containing polymer (SP1) comprising the polyaryl ether and the salt (S),
ii) pelletizing the first salt-containing polymer (SP1) provided in step i) to obtain a pelletized first salt-containing polymer (PSP1),
iii) contacting the pelletized first salt-containing polymer (PSP1) obtained in step ii) with the extractant (E) to obtain the salt-containing polymer (SP) comprising the polyaryl ether and residues of the salt (S), and a first salt-containing extractant (SE1) comprising the extractant (E) and a portion of the salt (S),
iv) heating the salt-containing polymer (SP) obtained in step iii) to a first temperature $T_1$ above the softening temperature $T_S$ of the polyaryl ether,
v) contacting the salt-containing polymer (SP) heated in step iv) with the extractant (E) to obtain the desalinated polymer (DP) comprising the polyaryl ether, and a second salt-containing extractant (SE2) comprising the extractant (E) and the residues of the salt (S).

If the first salt-containing polymer (SP1) comprises less than 10% by weight of the salt (S), preferably less than 8% by weight and especially preferably less than 6% by weight, based on the total weight of the first salt-containing polymer (SP1), there is no need to conduct steps i) to iv). Instead, only steps a) and b) are generally conducted. In this embodiment, the first salt-containing polymer (SP1) is the same as the salt-containing polymer (SP).

If the first salt-containing polymer (SP1), in contrast, comprises at least 6% by weight, preferably at least 8% by weight and especially preferably at least 10% by weight of the salt (S), steps i) to iv) are generally conducted. In that case, the first salt-containing polymer (SP1) is different than the salt-containing polymer (SP).

In step i), the first salt-containing polymer (SP1) is provided. Methods for providing the first salt-containing polymer (SP1) are known as such to those skilled in the art. Preferably, the first salt-containing polymer (SP1) is provided in step i) by a melt polymerization method.

The present invention thus also provides a process in which the first salt-containing polymer (SP1) is provided in step i) by a melt polymerization method.

The above-described details and preferences apply to the melt polymerization process.

The above details and preferences relating to the salt-containing polymer (SP) apply correspondingly to the first salt-containing polymer (SP1). When the first salt-containing polymer (SP1) is different than the salt-containing polymer (SP), i.e. when method steps i) to iii) are conducted, the first salt-containing polymer (SP1) comprises more salt (S) than the salt-containing polymer (SP).

In step ii), the first salt-containing polymer (SP1) provided in step i) is pelletized to obtain the pelletized first salt-containing polymer (PSP1). Methods for this purpose are known as such to those skilled in the art.

Preferably, step i) and step ii) are effected continuously. In this embodiment, the first salt-containing polymer (SP1) is preferably provided by a melt polymerization method, in which case the reactor used for the melt polymerization comprises an extruder by which the first salt-containing polymer (SP1) can be extruded after step i) and then pelletized in step ii). The pelletization can be effected, for example, as a strand pelletization or as an underwater pelletization.

In step ii), the first salt-containing polymer (SP1) is pelletized, for example, to a particle size in the range from 0.3 to 10 mm, preferably in the range from 0.4 to 6 mm and especially preferably in the range from 0.5 to 2 mm.

The pelletized first salt-containing polymer (PSP1) thus generally has a particle size in the range from 0.3 to 10 mm, preferably in the range from 0.4 to 6 mm and especially preferably in the range from 0.5 to 2 mm, determined by image analysis.

The present invention thus also provides a method in which the first salt-containing polymer (SP1) is pelletized in step ii) to a particle size in the range from 0.3 to 10 mm.

In step iii), the pelletized first salt-containing polymer (PSP1) obtained in step ii) is contacted with the extractant (E). The same details and preferences as described for step b) apply to the extractant (E).

Step iii) is also referred to as "pre-extraction". The terms "step iii)" and "pre-extraction" are used synonymously hereinafter.

Step iii) is typically conducted at a temperature below the glass transition temperature $T_G$ of the polyaryl ether. Preferably, step iii) is conducted below the softening temperature $T_S$ of the polyaryl ether.

Step iii) is generally conducted at a temperature in the range from 50 to 150° C., preferably in the range from 60 to 100° C. and especially preferably in the range from 70 to 100° C.

The absolute pressure in the reactor during process step iii) is preferably in the range from 1 to 10 bar, more preferably in the range from 1 to 7 bar, most preferably in the range from 1 to 5 bar.

Suitable reactors for step iii) are known as such to those skilled in the art. Suitable reactors are, for example, stirred tank reactors and tubular reactors. Preference is given in accordance with the invention to tubular reactors.

It is also preferable that the reactor used in step iii) can be heated from the outside to the temperature at which the pelletized first salt-containing polymer (PSP1) is contacted with the extractant (E).

According to the invention, the reactor can optionally also be equipped, for example, with centrifuges and/or filters in order to separate the first salt-containing extractant (SE1) obtained in step iii) from the salt-containing polymer (SP) obtained in step iii).

The pelletized first salt-containing polymer (PSP1) may take the form of a fixed bed in the reactor, such that the reactor used is a fixed bed reactor. It is likewise possible and preferable in accordance with the invention to use a countercurrent reactor in step iii).

Countercurrent reactors are known as such to those skilled in the art. In one embodiment of the present invention, the pelletized first salt-containing polymer (PSP1) can, for example, be passed continuously through the countercurrent reactor and the extractant (E) can be fed in from the opposite direction.

If step iii) is conducted in a fixed bed reactor, the extractant (E) is passed through. In general, the extractant (E) is passed through the reactor from the bottom upward or from the top downward. Preferably, the extractant (E) is passed through the reactor from the bottom upward.

If a countercurrent reactor is used, the pelletized first salt-containing polymer (PSP1) is generally introduced into the reactor continuously from the top and removed therefrom at the bottom, while the extractant (E) is simultaneously conducted into the reactor from the bottom and flows out at the top.

In step iii), the salt-containing polymer (SP) comprising the polyaryl ether and residues of the salt (S) and a first salt-containing extractant (SE1) comprising the extractant (E) and a portion of the salt (S) are obtained.

The first salt-containing extractant (SE1) comprises the extractant (E) and the portion of the salt (S) which has been removed from the pelletized first salt-containing polymer (PSP1). In general, the first salt-containing extractant (SE1) comprises 0.09% to 18% by weight of the salt (S), preferably 0.45% to 9% by weight of the salt (S) and especially preferably 0.9% to 5% by weight of the salt (S), based in each case on the total weight of the first salt-containing extractant (SE1).

"Residues of the salt (S)" are understood in accordance with the invention to mean 0.02% to 10% by weight, preferably 0.1% to 8% by weight and especially preferably 0.2% to 6% by weight of the salt (S), based in each case on the total weight of the salt-containing polymer (SP).

In other words, the salt-containing polymer (SP) obtained in step iii) comprises generally 0.02% to 10% by weight, preferably 0.1% to 8% by weight and especially preferably 0.2% to 6% by weight of the salt (S), based in each case on the total weight of the salt-containing polymer (SP).

It will be apparent that the salt-containing polymer (SP) obtained in step iii) comprises less salt (S) than the first salt-containing polymer (SP1) and the pelletized first salt-containing polymer (PSP1).

If the first salt-containing polymer (SP1) comprises less than 10% by weight, preferably less than 8% by weight and especially preferably less than 6% by weight of the salt (S), based on the total weight of the first salt-containing polymer (SP1), steps i) to iii) are generally not conducted.

In that case, the first salt-containing polymer (SP1) is used directly as salt-containing polymer (SP).

In step iv), the salt-containing polymer (SP) obtained in step iii) is heated to a first temperature $T_1$ above the softening temperature $T_S$, preferably above the glass transition temperature $T_G$, of the polyaryl ether.

In step iv), the salt-containing polymer (SP) is generally heated in a reactor. Suitable reactors in step iv) are the same reactors as described above for step a). Therefore, the same details and preferences as for the reactors in step a) apply to the reactors in step iv).

The salt-containing polymer (SP) can be heated by any methods known to those skilled in the art.

The details and preferences described above for the first temperature $T_1$ in step a) apply to the first temperature $T_1$ to which the salt-containing polymer (SP) is heated in step iv).

In step v), the salt-containing polymer (SP) heated in step iv) is contacted with the extractant (E). The same details and preferences as described above for step b) apply to the contacting of the salt-containing polymer (SP) heated in step iv) with the extractant (E).

In step v), the desalinated polymer (DP) comprising the polyaryl ether and a second salt-containing extractant (SE2) comprising the extractant (E) and residues of the salt (S) are obtained.

It will be apparent that the second salt-containing extractant (SE2) which is obtained in step v) is the same as the salt-containing extractant (SE) which is obtained in step b) when the first salt-containing polymer (SP1) is the same as the salt-containing polymer (SP).

In one embodiment of the present invention, the second salt-containing extractant (SE2) can be used as extractant (E) in method step iii).

It will be apparent that the desalinated polymer (DP) which is obtained in step b) or in step v) comprises less salt (S) than the first salt-containing polymer (SP1) and the salt-containing polymer (SP). In general, the desalinated polymer (DP) still comprises traces of the salt (S).

"Traces of the salt (S)" in the present case are understood to mean a salt content in the desalinated polymer (DP) of not more than 150 ppm by weight, preferably not more than 100 ppm by weight, especially preferably not more than 80 ppm by weight and most preferably not more than 50 ppm by weight of the salt (S), based in each case on the total weight of the desalinated polymer (DP).

In general, the desalinated polymer (DP) comprises 0.01 to 150 ppm by weight of the salt (S), preferably 0.1 to 100 ppm by weight, more preferably 1 to 80 ppm by weight and especially 5 to 50 ppm by weight of the salt (S), based in each case on the total weight of the desalinated polymer (DP).

In one embodiment of the present invention, the desalinated polymer (DP) comprises not more than 150 ppm by weight, preferably not more than 100 ppm by weight, especially preferably not more than 80 ppm by weight and most preferably not more than 50 ppm by weight of the salt (S), based in each case on the total weight of the desalinated polymer (DP).

The present invention thus also provides a method in which the desalinated polymer (DP) obtained in step b) comprises not more than 150 ppm by weight of the salt (S), based on the total weight of the desalinated polymer (DP).

The lower limit of the content of salt (5) in the desalinated polymer (DP) is generally 0.01 ppm by weight, preferably 0.1 ppm by weight, more preferably 1 ppm by weight and especially preferably 5 ppm by weight.

In an especially preferred embodiment, the desalinated polymer (DP) is essentially free of the salt (S). In the context of the present invention, "essentially free" means that the desalinated polymer (DP) comprises not more than 15 ppm by weight, preferably not more than 10 ppm by weight and especially preferably not more than 5 ppm by weight of the salt (S).

In one embodiment of the present invention, step b) can be repeated. In this case, it can be repeated once or else more than once. It is likewise possible to repeat step iii) and step v) once or more than once.

The desalinated polymer (DP) can be separated from the salt-containing extractant (SE) by methods known to those skilled in the art. For example, it can be separated from the salt-containing extractant (SE) by sedimentation.

It is also possible to dry the desalinated polymer (DP). Suitable methods for drying are in principle all methods known to those skilled in the art. For example, the desalinated polymer (DP) can be dried at elevated temperatures. Preference is given to temperatures in the range from 50 to 160° C., more preferably in the range from 100 to 150° C. The drying temperature is typically below the softening temperature $T_S$ of the polyaryl ether. The drying can optionally be conducted under reduced pressure.

The above-described details and preferences relating to the separation of the desalinated polymer (DP) from the salt-containing extractant (SE) apply to the separation of the desalinated polymer (DP) from the second salt-containing extractant (SE2).

When the salt-containing polymer (SP) has been prepared in a melt polymerization method, the salt-containing polymer (SP) and hence also the desalinated polymer (DP) does not comprise any aprotic polar solvent selected from the group consisting of N,N-dimethylformamide, N,N-dimethylacetamide, N-methylpyrrolidone, N-ethylpyrrolidone, dimethyl sulfoxide, dimethyl sulfone, sulfolane, diphenyl sulfone and mixtures thereof; the desalinated polymer (DP) preferably does not comprise any aprotic polar solvent.

The present invention thus also provides a desalinated polymer (DP) comprising 0 to 100 ppm by weight, preferably 0 to 20 ppm by weight and especially preferably 0 to 10 ppm by weight of an aprotic polar solvent selected from the group consisting of N,N-dimethylformamide, N,N-dimethylacetamide, N-methylpyrrolidone, N-ethylpyrrolidone, dimethyl sulfoxide, dimethyl sulfone, sulfolane, diphenyl sulfone and mixtures thereof, most preferably no aprotic polar solvent, and comprising less than 150 ppm by weight, preferably less than 100 ppm by weight, more preferably less than 80 ppm by weight and most preferably less than 50 ppm by weight of the salt (S), where the ppm by weight are based in each case on the total weight of the desalinated polymer (DP).

The present invention thus also provides a desalinated polymer (DP) obtainable by the method of the invention.

The present invention also provides a desalinated polymer (DP) obtainable by the method of the invention, comprising 0 to 100 ppm by weight of an aprotic polar solvent selected from the group consisting of N,N-dimethylformamide, N,N-dimethylacetamide, N-methylpyrrolidone, N-ethylpyrrolidone, dimethyl sulfoxide, dimethyl sulfone, sulfolane, diphenyl sulfone and mixtures thereof, and comprising less than 150 ppm by weight of the salt (S), where the ppm by weight are each based on the total weight of the desalinated polymer (DP).

The desalinated polymers (DP) obtainable by the method of the invention preferably have an apparent melt viscosity at 350° C./1150 s$^{-1}$ of 100 to 1000 Pa s, preferably of 150 to 300 Pa s and especially preferably of 150 to 275 Pa s.

The melt viscosity was determined by means of a capillary rheometer. The apparent viscosity was determined at 350° C. as a function of the shear rate in a capillary viscometer (Götffert Rheograph 2003 capillary viscometer) with a circular capillary of length 30 mm, a radius of 0.5 mm, a nozzle inlet angle of 180°, a diameter of the reservoir vessel for the melt of 12 mm and with a preheating time of 5 minutes. The values reported are those determined at 1150 s$^{-1}$.

The viscosity numbers of the polymers (DP) desalinated by the method of the invention are generally in the range from 20 to 120 mL/g, preferably from 30 to 100 mL/g and especially preferably from 35 to 95 mL/g, determined by Ubbelohde viscosity number measurement of a 0.01 g/mL solution of the salt-containing polymer (SP) in a 1:1 phenol/1,2-dichlorobenzene mixture in accordance with DIN 51562.

The present invention also provides a method for desalinating a salt-containing polymer (SP) comprising a polyaryl ether having a glass transition temperature $T_G$ and a salt (S), comprising the steps of
a) providing the salt-containing polymer (SP) at a first temperature $T_1$ above the glass transition temperature $T_G$ of the polyaryl ether,
b) contacting the salt-containing polymer (SP) provided in step a) with an extractant (E) to obtain a desalinated polymer (DP) comprising the polyaryl ether, and a salt-containing extractant (SE) comprising the extractant (E) and the salt (S).

The invention is elucidated in detail by examples hereinafter, without restricting it thereto.

EXAMPLES

Examples 1 and 2

Polyether sulfone (PESU, Ultrason E) was prepared proceeding from bisphenol S as component (a1) and 4,4"-dihalodiphenyl sulfone as component (a2) in the presence of potassium carbonate as carbonate component (C) in a melt polymerization process.

The polyether sulfone obtained was pelletized and extracted with water at 80° C. for 24 hours. The salt content of the salt-containing polymer (SP) thus obtained was less than 1% of the original concentration of the salt (S). Subsequently, the salt (5) (potassium chloride) was extracted from the salt-containing polymer (SP) obtained in an autoclave with water at a temperature of 250° C. In each case, 30 g of salt-containing polymer (SP) were extracted with water.

For the different examples, the water was changed after different periods of time. In example 1, the water was changed after 7, 23, 29 and 48 hours; in example 2, the water was changed every two hours.

The resulting salt content of the desalinated polymer (eP) as a function of the extraction time from example 1 is reported in table 1, and that from example 2 in table 2. Likewise reported in tables 1 and 2 is the conductivity of the water with which the salt (S) was extracted,

TABLE 1

| Time [h] | Conductivity [mS] | Chlorine [g/100 g] | Chloride {g/100 g} | Potassium [g/100 g] |
|---|---|---|---|---|
| 8 | 16.18 | | | |
| 25 | 1.72 | 0.24 | 0.042 | 0.09 |
| 31 | 0.24 | | | |
| 49 | 0.21 | 0.17 | 0.01 | 0.013 |

TABLE 2

| Time [h] | Conductivity [mS] | Chlorine [g/100 g] | Chloride {g/100 g} | Potassium [g/100 g] |
|---|---|---|---|---|
| 2 | 16.15 | | | |
| 4 | 4.12 | | | |
| 6 | 0.70 | | | |
| 8 | 0.24 | | | |
| 10 | 0.11 | | | |
| 12 | 0.04 | | | |
| 14 | 0.04 | 0.17 | 0.002 | 0.037 |

The invention claimed is:
1. A method for desalinating a salt-containing polymer (SP) comprising a polyaryl ether having a softening temperature $T_S$ and a salt (S), comprising the steps of
a) providing the salt-containing polymer (SP) at a first temperature $T_1$ above the softening temperature $T_S$ of the polyaryl ether,
b) contacting the salt-containing polymer (SP) provided in step a) with an extractant (E) to obtain a desalinated polymer (DP) comprising the polyaryl ether, and a salt-containing extractant (SE) comprising the extractant (E) and the salt (S),
wherein step a) comprises the following steps:
i) providing a first salt-containing polymer (SP1) comprising the polyaryl ether and the salt (S),
ii) pelletizing the first salt-containing polymer (SP1) provided in step i) to obtain a pelletized first salt-containing polymer (PSP1),
iii) contacting the pelletized first salt-containing polymer (PSP1) obtained in step ii) with the extractant (E) to obtain the salt-containing polymer (SP) comprising the polyaryl ether and residues of the salt (S), and a first salt-containing extractant (SE1) comprising the extractant (E) and a portion of the salt (S), iv) heating the salt-containing polymer (SP) obtained in step iii) to a first temperature $T_1$ above the softening temperature $T_S$ of the polyaryl ether, and wherein step b) comprises the following step:

v) contacting the salt-containing polymer (SP) heated in step iv) with the extractant (E) to obtain the desalinated polymer (DP) comprising the polyaryl ether, and a second salt-containing extractant (SE2) comprising the extractant (E) and the residues of the salt (S), wherein the first salt-containing polymer (SP1) is provided in step i) by a melt polymerization method.

2. The method according to claim 1, wherein the salt-containing polymer (SP) is contacted with the extractant (E) in step b) at a second temperature $T_2$ above the softening temperature $T_S$ of the polyaryl ether.

3. The method according to claim 2, wherein the second temperature T2 at which the salt-containing polymer (SP) is contacted with the extractant (E) in step b) is in the range from 160 to 300° C.

4. The method according to claim 1, wherein the first temperature $T_1$ in step a) is within a range from 160 to 300° C.

5. The method according to claim 1, wherein the first temperature $T_1$ is in the range from 1 to 100° C. above the softening temperature $T_S$ of the polyaryl ether.

6. The method according to claim 1, wherein the softening temperature $T_S$ of the polyaryl ether is in the range from 150 to 230° C.

7. The method according to claim 1, wherein the extractant (E) in step b) comprises water.

8. The method according to claim 1, wherein the desalinated polymer (DP) obtained in step b) comprises not more than 150 ppm by weight of the salt (S), based on the total weight of the desalinated polymer (DP).

9. The method according to claim 1, wherein the first salt-containing polymer (SP1) is pelletized in step ii) to a particle size in the range from 0.3 to 10 mm.

10. The method according to claim 1, wherein the polyaryl ether is a polyaryl ether sulfone.

11. The method according to claim 1, wherein the salt (S) comprises potassium chloride and/or sodium chloride.

* * * * *